United States Patent

Voydeville

Patent Number: 6,042,612
Date of Patent: Mar. 28, 2000

[54] NON-DISLOCATABLE LOW-WEAR HIP PROSTHESIS

[76] Inventor: Gilles Voydeville, 90, quai Claude-le-Lorrain, Nancy 54000, France

[21] Appl. No.: 09/117,680

[22] PCT Filed: Feb. 3, 1997

[86] PCT No.: PCT/FR97/00213

§ 371 Date: Oct. 7, 1998

§ 102(e) Date: Oct. 7, 1998

[87] PCT Pub. No.: WO97/27827

PCT Pub. Date: Aug. 7, 1997

[30] Foreign Application Priority Data

Feb. 2, 1996 [FR] France .................................. 96 01308

[51] Int. Cl.[7] .................................. A61F 2/34; A61F 2/36
[52] U.S. Cl. .................................. 623/23; 623/18; 623/22
[58] Field of Search .................................. 623/181, 19, 22, 623/23

[56] References Cited

U.S. PATENT DOCUMENTS

| | | | |
|---|---|---|---|
| 3,916,451 | 11/1975 | Buechel et al. | 623/19 |
| 4,159,544 | 7/1979 | Termanini . | |
| 4,408,360 | 10/1983 | Keller | 623/18 |
| 4,798,610 | 1/1989 | Averill et al. | 623/22 |
| 4,950,299 | 8/1990 | Noiles | 623/22 |
| 5,181,929 | 1/1993 | Prats et al. | 623/23 |
| 5,593,445 | 1/1997 | Waits | 623/18 |
| 5,879,390 | 3/1999 | Kubein-Maesenburg et al. | 623/20 |

FOREIGN PATENT DOCUMENTS

| | | |
|---|---|---|
| 0 412 438 | 2/1991 | European Pat. Off. . |
| 0 461 019 | 12/1991 | European Pat. Off. . |
| 0 639 357 | 2/1995 | European Pat. Off. . |
| 32 00 340 | 9/1982 | Germany . |
| 93 12 150 | 12/1993 | Germany . |
| 44 01 815 | 8/1994 | Germany . |
| WO 93/03687 | 3/1993 | WIPO . |

*Primary Examiner*—Bruce E. Snow
*Attorney, Agent, or Firm*—Young & Thompson

[57] ABSTRACT

This hip prosthesis includes a femoral stem (3), a spherical head (6) designed to fit over a neck (5) of the femoral stem, and a metal socket (1) in which the head can articulate; a cup (7) is inserted between the head (6) and the socket, the head and the cup being made of ceramic or similar material having a low coefficient of friction, the head being articulated on the cup; the cup itself is articulated in a plastic socket (8) fixed in the metal socket (1). This prosthesis thus comprises a double articulation, on the one hand between its head (6) and the cup (7), and on the other hand between the cup (7) and the polyethylene socket (8), the first ceramic-ceramic articulation being the one principally stressed. For this reason, the wear of the polyethylene socket (8) produces extremely little debris, which considerably reduces the risks of separation and very substantially prolongs the total lifetime of the prosthesis. This prosthesis has low-wear properties.

8 Claims, 1 Drawing Sheet

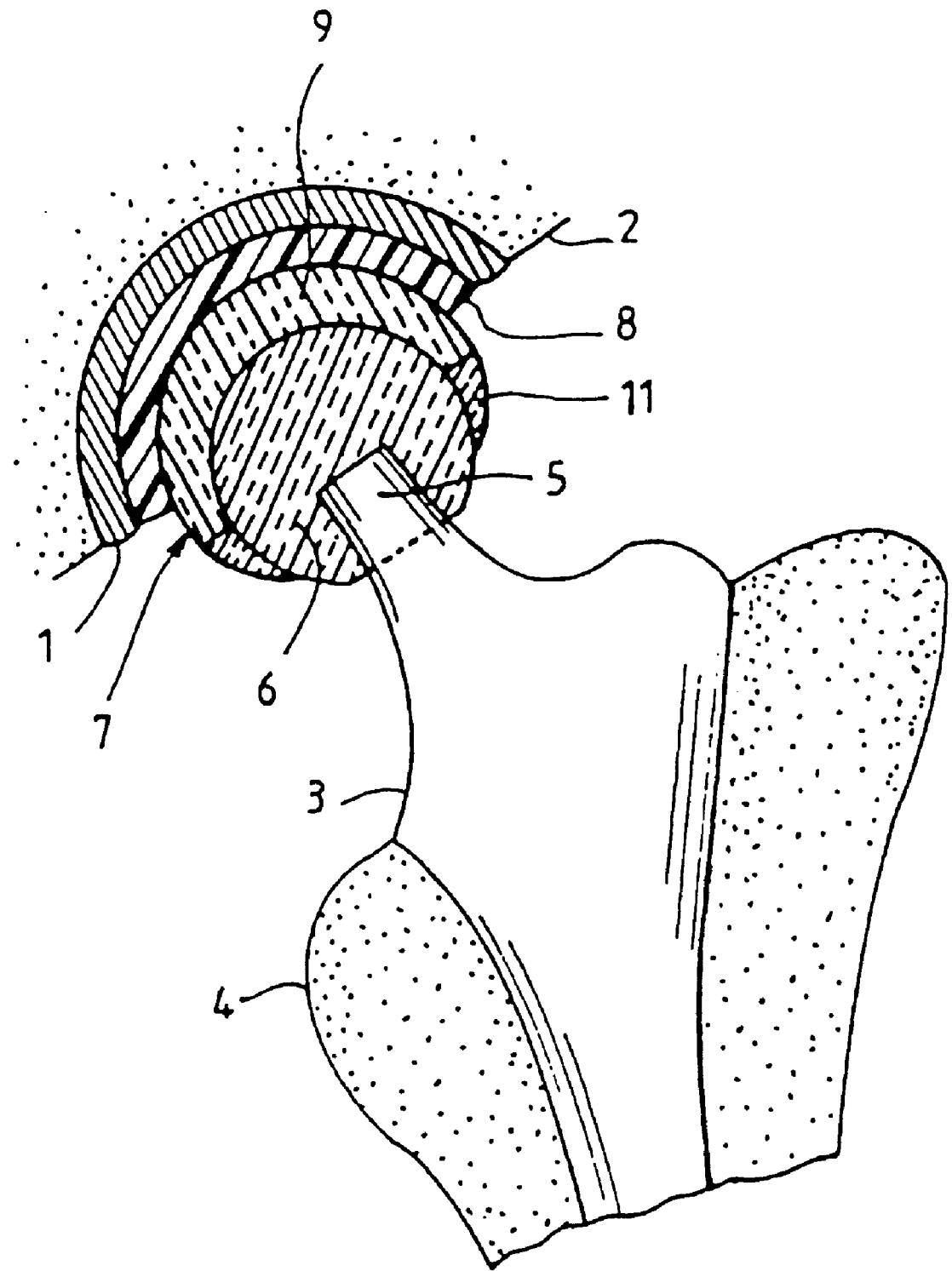

NON-DISLOCATABLE LOW-WEAR HIP PROSTHESIS

FIELD OF THE INVENTION

The present invention relates to a hip prosthesis comprising a femoral stem, a spherical head designed to fit over a neck of the femoral stem, and a metal socket in which the head can articulate, and a cup inserted between the head and the socket.

BACKGROUND OF THE INVENTION

As is known, the heads of femoral stems of hip prostheses are generally articulated on a polyethylene component lodged in the metal socket, which itself is impacted in the osseous wall of the acetabular cavity. The polyethylene component forms a socket internal to the metal socket and fixed to the latter. Now, the frictions between the metal or ceramic head and the polyethylene insert component cause certain problems. In addition, these prostheses present risks of dislocation.

The problem caused by the appearance of polyethylene debris resulting from the friction of the head of the prosthesis against the polyethylene socket is well known. This wear leads to the formation of polyethylene micro-debris which itself provokes a macrophage reaction, which itself leads to the production of a membrane disposed between the implants and the bone, this membrane itself being a cause of separation.

The problem of hip dislocation is substantially different. It is known that the hip prostheses comprising a head of large diameter, that is to say of at least 32 mm, are unlikely to dislocate and are relatively stable; the prostheses with a greater diameter, for example of the MAC KEE, FARRART or THOMSON types, are even less dislocatable. Moreover, for some time now hip prosthesis heads have been used with a considerably smaller diameter, for example 28 mm, in order to reduce wear, since the coefficient of friction between such a head and the polyethylene is less than with a head which has a greater diameter.

However, this has not sufficed to eliminate wear and has led to another problem, namely that of the instability of the hips. The reason is that as the coefficient of friction is lower, the hip is more dislocatable, particularly in the period immediately following surgery.

Ceramic-ceramic friction pairings are also known and afford advantages. However, these pairings lead to other difficulties, especially risks of separation and dislocation.

The document EP-A-0 461 019 describes a hip prosthesis comprising a spherical head articulated in an elastic female part of a cup articulated in a socket. The head can leave the elastic female part, which renders the prosthesis dislocatable and thus constitutes a very considerable disadvantage.

Finally, prostheses are known which include a cup of large diameter which is impacted on a metal head with interposition of flexible polyethylene in order to permit the impaction and retention on the metal head. This system thus still entails metal-polyethylene wear. Moreover, this type of prosthesis causes cotyloid inflammation because they are arranged in osseous sockets, and one then observes an osseous reaction to the metal implant situated opposite.

SUMMARY OF THE INVENTION

The object of the invention is to make available a hip prosthesis designed to remedy these various disadvantages.

According to the invention, the hip prosthesis comprises a cup inserted between the head and the socket, the said head and the cup being made of a material having a low coefficient of friction, the head being articulated on the cup, and the cup itself being articulated in a plastic socket fixed in the metal socket.

Thus the head, advantageously made of ceramic or equivalent material, which rests on the neck, is articulated in a cup which is also made of ceramic or equivalent, including, according to one feature of the invention, means for connecting it to the head in a non-removable manner.

The cup can advantageously be made up of a substantially hemispherical part and of a ring formed by a portion of a sphere, fixed to the hemispherical part in order to prevent the latter separating from the head.

Thus, a ceramic head is formed which is movable inside a second incomplete ceramic head formed by a cup which can be described as "retentive". For this cup to be "retentive", it has to extend over more than half a sphere including the complementary ring.

The latter can be fixed to the hemispherical part by any appropriate means, in particular adhesive bonding or soldering. The soldering can be done using gold, either at the works or in the operating theatre, it also being possible for a screw connection assembly to be provided. The most reliable method appears to be soldering with gold, carried out during production.

The prosthesis according to the invention permits very low friction, particularly ceramic-ceramic friction, producing very few products of degradation, by virtue of an extremely low coefficient of friction, and it is thus very low-wearing. Indeed, the ceramic-ceramic pairing is the one which to date has the lowest coefficient of friction known.

In addition, the ceramic cup is advantageously non-disconnectable from the ceramic head, since the soldering is carried out solidly at the works.

Moreover, the double head formed by the ceramic head and the cup in which it is articulated has a large external diameter, which has the advantage of being unlikely to dislocate.

This arrangement is still subject to wear, but because the articulation always tends to occur at the point where there is the lowest coefficient of friction, the invention makes it possible to realize the main articulation between the head and the associated cup in which it is confined. Indeed, the second articulation between the cup and the polyethylene socket only intervenes at extreme amplitudes, i.e. rarely. Thus, the rarity of these articulations means less polyethylene debris and thus considerably reduces the risks of separation by macrophage reaction.

Other features and advantages of the invention will be evident from the description which is given hereinafter, with reference being made to the attached drawing which illustrates one embodiment thereof by way of a non-limiting example.

BRIEF DESCRIPTION OF THE DRAWINGS

The single FIGURE is a mid-sectional mid-elevation view of an embodiment of the hip prosthesis according to the invention.

DETAILED DESCRIPTION OF THE INVENTION

The hip prosthesis represented in the single FIGURE comprises a socket 1 which can be anchored by impaction in the acetabular cavity of the iliac bone 2 of a patient, a femoral stem 3 which can be anchored in the upper end of a femur 4, the stem 3 ending in a neck 5.

The prosthesis also comprises a spherical head 6 in which a bore is formed with suitable dimensions to allow the head 6 to cover the neck 5, and a cup 7 inserted between the head 6 and a plastic socket 8, preferably of polyethylene. This socket 8 is fixed on the inner wall of the socket 1, which is made of metal, preferably titanium.

The cup 7 comprises means for connecting it to the head 6 in a non-removable manner. In the embodiment shown, the cup 7 is thus made up of a substantially hemispherical part 9, designed to receive the corresponding spherical head 6, and of a ring 11 formed by a portion of a sphere. The ring 11 is fixed to the hemispherical part 9 by any appropriate means, for example screwing or adhesive bonding or soldering, especially with gold, as indicated above. This joining is carried out after first introducing the head 6 into the hemispherical part 9.

The cup 7 thus formed therefore occupies a greater volume than half a sphere, in such a way that it can no longer be separated from the head 6, which remains articulated freely inside the cup 7. By way of example, the ring 11 can be formed by a portion of about ¼ or ⅙ or ⅛ of a sphere.

The head 6 and the cup 7 are advantageously made of ceramic or other material having a very low coefficient of friction, for example a metal compound with a very low coefficient of friction, with ion implantation. The prosthesis formed in this way thus has a double articulation, namely a first articulation between the head 6 and the cup 7, and a second articulation between the cup 7 and the plastic socket 8, which affords the advantages set out above.

By way of a non-limiting numerical example, the head 6 can have a diameter of 22, 26 or 28 mm, the appropriate maximum diameter seeming to be 28 mm for reasons of space. The thickness of the cup 7 can be about 5 mm, so that its diameter is 22, 26 or 28 mm+(5×2), i.e. 32, 36 or 38 mm. A head with a double articulation is thus formed whose external diameter is unlikely to dislocate.

The polyethylene socket 8 preferably has a minimum thickness of 6 mm, the socket 1, preferably of titanium, having a thickness of 1 or 2 mm only, in order to take up little space.

Finally, the prosthesis reaches an external diameter (socket 1) of 50 mm diameter, which can be achieved in practically 98% of cases.

For the remaining 2%, the prosthesis can comprise a head 6 with a diameter of 22 mm only, which, added to 5×2 mm supplementary diameter of the cup 7, gives the latter an external diameter of 32 mm. By adding 6 mm of thickness for the socket 8 thereto, one arrives at 44 mm, then with 2 mm thickness in total for the socket 1, a prosthesis is obtained having a total external diameter of 46 mm.

The double articulation is thus made up of a "retentive" non-dislocatable articulation and of a non-retentive articulation with the polyethylene socket; a prosthesis is thus obtained which is less dislocatable than the conventional prostheses of 22, 26, 28 mm diameter.

The prosthesis according to the invention thus comprises a head 6 which is not detachable from the cup 7 on which it is articulated, and whose movements do not produce any debris or any deterioration on account of the ceramic or equivalent materials used. The second articulation between the cup 7 and the socket 8 functions very little because of the preceding articulation which has a coefficient of friction lower than that of the cup and of the socket 8. For this reason, the debris produced on this latter articulation is so small that it is possible to bring the effective lifetime of the prosthesis from 15 years to 20 or 25 years.

What is claimed is:

1. Hip prosthesis comprising:
    a femoral stem having a first end adapted to be implanted in a femur, and a neck at an opposite second end;
    a femoral head comprising a substantially spherical body having an outer surface, and a bore structured and arranged to fit over the neck;
    a cup having an outer surface, and an inner surface structured and arranged to fit over the outer surface of the head; the head being pivotable relative to the cup;
    said head and said cup being made of a material having a low coefficient of friction and selected from the group consisting of a ceramic and a metal compound with ion implantation;
    a metal socket having an inner surface, and an outer surface intended to be anchored in an acetabular cavity;
    a plastic socket having an outer surface fixed to the inner surface of the metal socket, and an inner surface structured and arranged to fit over the outer surface of the cup; the cup being pivotable relative to the plastic socket; and
    said cup being structured and arranged for non-removable attachment to said head.

2. Prosthesis according to claim 1, wherein the cup and the head are made of a ceramic material.

3. Prosthesis according to claim 1, wherein the cup is made up of a substantially hemispherical part and of a ring formed by a portion of a sphere, fixed to the hemispherical part in order to prevent the hemispherical part from separating from the head.

4. Prosthesis according to claim 3, wherein the ring is fixed to the hemispherical part by one of adhesive bonding and soldering.

5. Prosthesis according to claim 3, wherein the ring constitutes a portion of about one quarter of a sphere.

6. Prosthesis according to claim 3, wherein the ring constitutes a portion of about one sixth of a sphere.

7. Prosthesis according to claim 3, wherein the ring constitutes a portion of about one eighth of a sphere.

8. Prosthesis according to claim 1, wherein the plastic socket is made of polyethylene, and the metal socket is made of titanium.

* * * * *